United States Patent [19]

Hagenimana et al.

[11] Patent Number: 5,525,154
[45] Date of Patent: Jun. 11, 1996

[54] METHOD FOR THE HYDROLYSIS OF STARCHY MATERIALS BY SWEETPOTATO ENDOGENOUS AMYLASES

[75] Inventors: Vital Hagenimana, Nairobi, Kenya; Ronald E. Simard, Sainte-Foy; Louis-Philippe Vézina, Neuville, both of Canada

[73] Assignees: Universite Laval; Agriculture and Agri-Food Canada, both of Quebec, Canada

[21] Appl. No.: 334,198

[22] Filed: Nov. 4, 1994

[51] Int. Cl.$^6$ .................................................. C08B 30/00
[52] U.S. Cl. ................... 127/66; 127/30; 127/36; 127/67; 127/70; 127/71; 127/44
[58] Field of Search ................... 127/30, 66, 36, 127/44, 56, 67, 70, 71

[56] References Cited

U.S. PATENT DOCUMENTS

| | | | |
|---|---|---|---|
| 116,597 | 7/1871 | Hutchins | 127/66 |
| 1,156,801 | 10/1915 | Moore | 127/66 |
| 1,735,976 | 11/1929 | Riemann | 127/66 |
| 2,443,897 | 6/1948 | Dexter et al. | 127/66 |
| 3,813,297 | 5/1974 | Shaw, Jr. | 127/66 |
| 3,922,200 | 11/1975 | Walon et al. | 195/31 R |
| 4,113,509 | 9/1978 | Leach et al. | 127/29 |
| 4,155,884 | 5/1979 | Hughes | 127/36 |
| 4,566,909 | 1/1986 | Yong et al. | 127/33 |
| 4,591,560 | 5/1986 | Kainuma et al. | 435/96 |
| 5,188,956 | 2/1993 | Nanmori et al. | 435/200 |

OTHER PUBLICATIONS

Blakeney, A. B. et al., 1980, J. Sci. Food Agric., 31: 889–897 month not available.
Hagenimana, V. et al., 1992, J. Agric. Food Chem., 40: 1777–1783 month not available.
Maeda, I. et al., 1978, Agric. Biol. Chem., 42(2): 259–267 month not available.
Rose, R. et al., 1991, J. Agric. Food Chem., 39: 2–11 month not available.
Walter, W. M., Jr. et al., 1975, J. Food Sci., 40: 793–796 month not available.

Primary Examiner—Paul Lieberman
Assistant Examiner—Patricia L. Hailey
Attorney, Agent, or Firm—Klauber & Jackson

[57] ABSTRACT

The present invention relates to a method for the hydrolysis of sweetpotato starch which comprises the steps of: a) separating outer and starchy inner tissues of sweetpotato roots; b) heating the separated starchy inner tissues of step a) for a time sufficient for obtaining a suitable slurry; c) preparing an amylase crude extract from sweetpotato roots outer tissues of step a); and d) incubating the slurry of step b) with the extract of step c) for a time sufficient for the complete hydrolysis of starch.

6 Claims, 8 Drawing Sheets

METHOD FOR THE HYDROLYSIS OF STARCHY MATERIALS BY SWEETPOTATO ENDOGENOUS AMYLASES

BACKGROUND OF THE INVENTION

1. Field of the Invention

The invention relates to a method for the hydrolysis of starchy materials based on the use of amylase extracted from sweetpotato root outer tissues.

2. Description of Prior Art

Sweetpotato, a high starch content crop, is considered as a potential agricultural source of maltodextrin, syrup, and glucose conversion. Recent interest in energy conservation and in renewable energy sources has focused considerable attention to starch hydrolysis in glucose, maltose, and dextrins by microbial amylases. Many exciting changes happened within the food industry as a result of improvements and innovations in the use of these enzymes. Although many more unique applications are being found, the cost of manufacturing and subsequently the cost-effectiveness of enzymes and the recent ecological worry presented a barrier.

However, in addition to high starch, sweetpotato roots have a high content of amylases. The native amylases have important and well-documented influences on sweetpotato root storage and processing (Walter, W. M., Jr. et al., 1975, J. Food Sci., 40: 793–796). It is known that in baked sweetpotato roots, endogenous amylases hydrolyze part of the starch into maltose and longer chain polysaccharides, resulting in a sweet taste. Nevertheless, baking temperature is sufficient enough to rapidly inactivate plant amylases, and limits the starch hydrolysis.

Raw sweetpotato starch is less susceptible to sweetpotato amylase digestion than boiled starch granules (Hagenimana, V. et al., 1992, J. Agric. Food Chem., 40: 1777–1783), and sweetpotato root mashes held a long time at temperatures from 30° to 80° C. do not gain in soluble solids or sugars but their starch retrograded suggesting the insufficient reduction in chain length of starch components. The utilization of endogenous amylases in sweetpotato processing should involve heating roots or their puree above 60° C. to gelatinize the starch fraction and to facilitate amylase action.

In starch hydrolysis materials such as maltodextrin, syrups, glucose, etc. from a granular starch feedstock, it is conventional practice to first subject an aqueous slurry of said granular starch material to a cooking or pasting operation, which is typically conducted at a temperature of from about 60° C. to about 180° C., and to thereafter convert the resulting cooked or pasted starch material to the desired starch hydrolysate product (e.g. typically maltodextrin, syrup or glucose) via one or more acid and/or enzyme hydrolysis operations.

In the case of enzyme-based hydrolysis operations, the cooked or pasted starch is typically treated for a relatively short period of time (e.g., 1 to 4 hours) under mildly acidic conditions (e.g., generally at a pH of about 6.0) and at a relatively high temperature (e.g., up to about 100° C.) with bacterial thermostable α-amylase enzyme in order to convert said starch slurry to maltodextrin. Such treatment is generally referred to in the art as "thinning" reaction. In the event that the maltodextrin thus formed is the desired end-product, the crude hydrolysis reaction product is purified or used as such. On the other hand, if the desired ultimate endproduct is syrup, the aforementioned maltodextrin material is subjected to further hydrolysis to convert said maltodextrin material to the desired syrup product. This latter hydrolysis operation is commonly referred to in the art as a "saccharification" process or operation. When said saccharification operation is performed via acid hydrolysis techniques, it is typically conducted using a strong mineral acid such as hydrochloric or sulfuric acid; at a pH in the range of from about 1 to about 2; at a temperature in the range of from about 90° C. to about 180° C.; and for a time period or reaction time of from about 0.1 to about 2 hours.

The use of endogenous sweetpotato amylases in hydrolysis of starch requires two conditions: first, starch gelatinization prior to hydrolysis and secondly, preservation of endogenous amylase activities during gelatinization.

α-amylase plays a major role in the digestion of starch and the combined action of α- and β-amylases is more effective than the action of α- or β-amylase alone (Maeda, I. et al., 1978, Agric. Biol. Chem., 42: 259–267). The ubiquitous distribution of β-amylases throughout the root and the localization of α-amylase in the outer layers of the root was recently reported (Hagenimana, V. et al., 1992, J. Agric. Food Chem., 40: 1777–1783).

It would be highly desirable to optimize the use of the endogenous amylases during processing of starchy materials. To do so, it was hypothesized that the outer tissue extract of sweetpotato containing both α- and β-amylases would be used to hydrolyze starch without adding exogenous amylases.

SUMMARY OF THE INVENTION

One aim of the present invention is to optimize the use of the endogenous amylases during processing of starchy materials.

Another aim of the present invention is to separate mechanically the enzyme source in the outer root tissues and the starch source from the core of sweetpotato roots.

Another aim of the present invention is to utilize the outer tissue extract of sweetpotato containing both α- and β-amylases to hydrolyze parenchymatous sweetpotato root starch without adding exogenous amylases.

By proper control of the starch-to-sugar or starch-to-soluble solids ratio in starchy puree through enzymatic starch conversion, a finished product of superior quality can be produced with greater efficiency and with improved flavor and handling characteristics.

Another aim of the present invention is to provide a process whereby the starch-sugar ratio can be readily controlled to the desired level by utilizing the natural amylase system in the roots of sweetpotatoes without addition of a commercial mixture of α- and β-amylases obtained from other sources to the puree.

In accordance with the present invention there is provided a method for the hydrolysis of sweetpotato starch in puree which comprises the steps of:

a) separating outer and starchy inner tissues of sweetpotato roots;

b) heating the separated starchy inner tissues of step a) for a time sufficient for obtaining a suitable starch slurry;

c) preparing an amylase crude extract from sweetpotato roots outer tissues of step a); and d) incubating the slurry of step b) with the extract of step c) for a time sufficient for the complete hydrolysis of said starch slurry.

DETAILED DESCRIPTION OF THE INVENTION

Storage sweetpotato roots are very starchy and in vitro activity measurements indicate that they contain high amounts of extractable amylolytic enzymes. Amylolytic protein distribution within the root indicates that $\alpha$-amylase is localized in the outer layers of the root while $\alpha$-amylase is ubiquitous throughout the root and therefore $\alpha$- and $\beta$-amylases can be mechanically separated from starchy portion.

In accordance with the present invention, $\alpha$- and $\beta$-amylases are extracted from the outer tissue by mechanical separation, and are incubated with starchy materials (e.g. inner portion from sweetpotato roots) which have been gelatinized by heating appropriately tempered. With this process, incubation at 50°–70° C. for about 30 min. to about 2 h. converted up to about 70% of insoluble starch into low molecular weight products and slurries containing up to 75% sugars on a dry weight basis were obtained. Glucose level in slurry could be increased fourfold after 30 to about 60 min. at 40° to 80° C. for both varieties analyzed. Maltose that was absent in non-heated slurry, showed a significant increase with incubation at 40°–80° C., and its level represented up to 40% of slurry dry matter after about 30 min. to about 2 h. incubation. Along with maltose, various oligodextrins also absent in non-heated sweetpotato slurry appeared with incubation.

The present invention will be more readily understood by referring to the following example which is given to illustrate the invention rather than to limit its scope.

EXAMPLE I

Starch hydrolysis of sweetpotato

Plant material

Regal and White Delight sweetpotatoes were grown in a greenhouse for 160 days. Sweetpotato roots were held at about 13° to about 16° C., 85–90% RH, for about 1 to 9 months.

Processing

Figure 1:
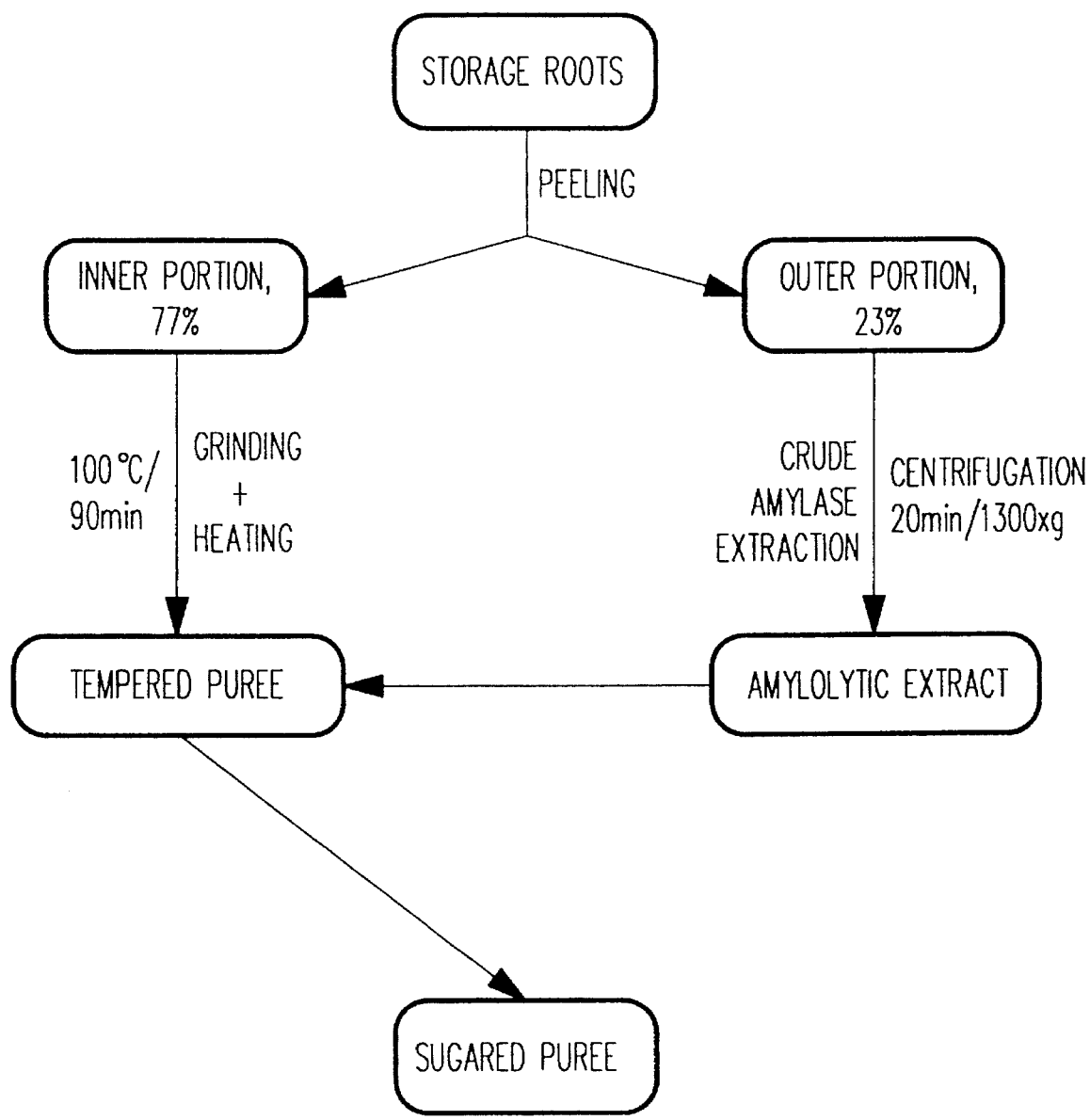
FIG. 1 illustrates a schematic process of sweetpotato starch digestion by endogenous amylases.

A schematic of the process is depicted in FIG. 1. The roots were washed and hand peeled (mean amount removed represented 10–30%); the peeled outer layer contained all of the cortical region (about 0.1 to 0.5 cm deep) which included the periderm, laticifer and cambium layers. The inner portion was the remaining tissue and represented the starchy materials. The appropriate sections were combined from all the roots, chopped, and homogenized in a Waring™ blender at pH 4.0–8.0. The homogenized inner portion puree was maintained at 60°–100° C. for 30 min. to about 2 h. in a water bath to gelatinize the starch and allowed to cool to appropriate digestion temperature that was about 30°–75° C. The outer portion puree was centrifuged for about 5 min. to about 1 h. at about 500×g to about 13,000×g. The precipitate was added to the inner portion slurry and the supernatant was considered as amylase extract. To the heated inner portion slurry that was first tempered at appropriate digestion temperature which was between 30° and 75° C., was added amylase extract.

Figure 2A:
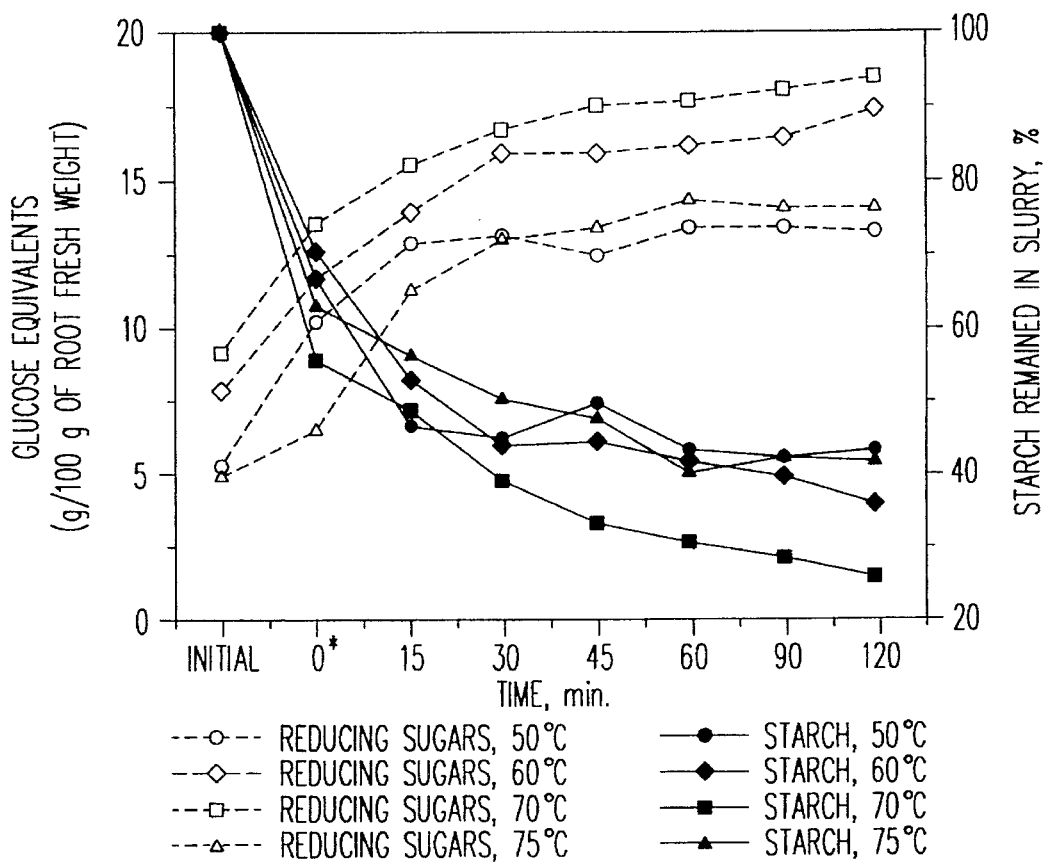
FIG. 2 illustrates the changes in starch and reducing sugars content during incubation of a slurry from the heated inner portion with extract from the outer tissue for sweetpotato Regal (A) and White Delight (B) varieties.
Figure 2B:
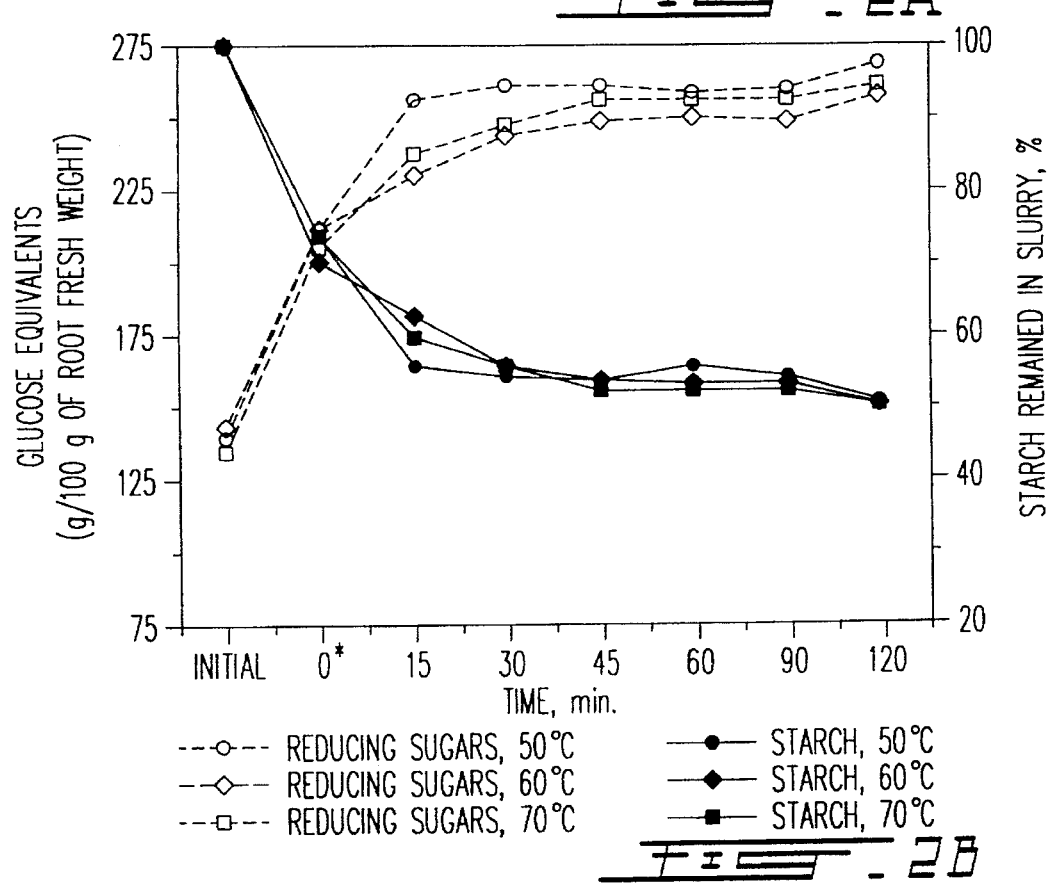
Figure 3A:
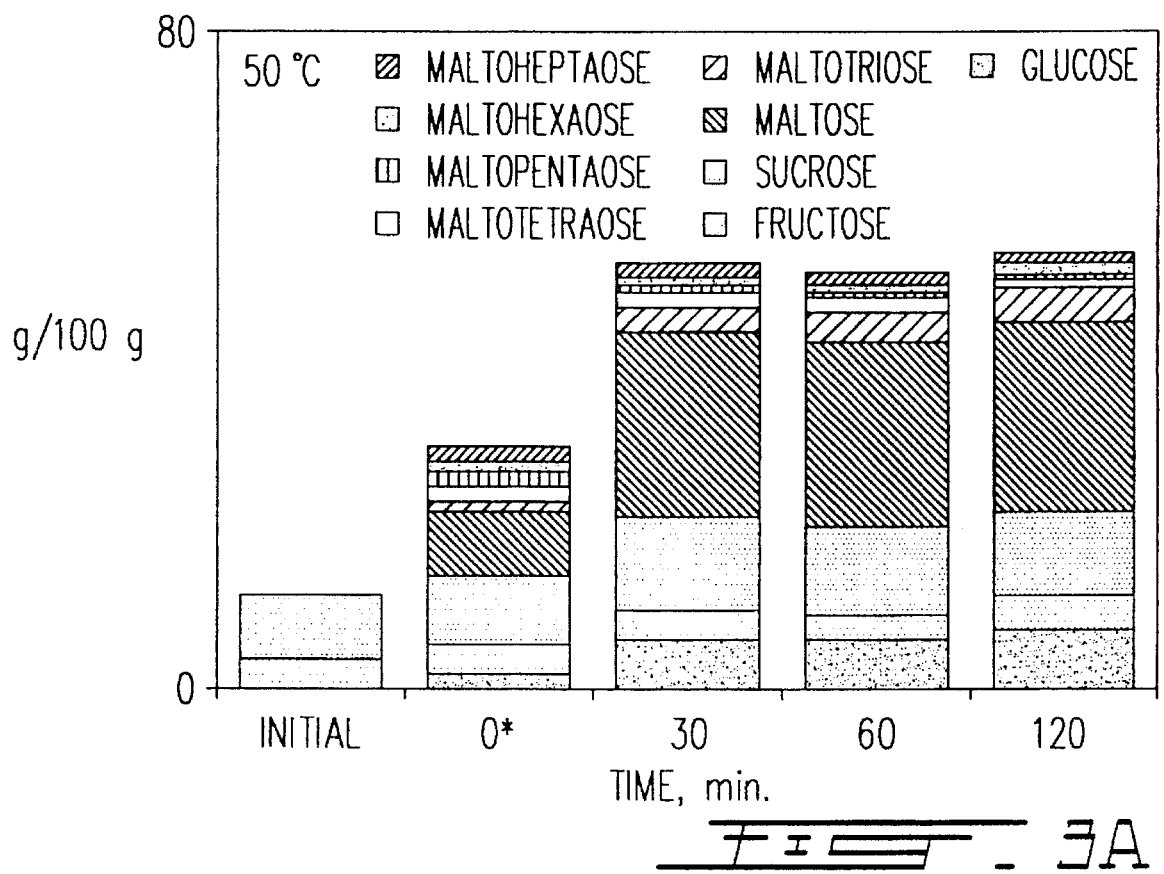
FIG. 3 illustrates the changes in sugar and oligodextrin content during digestion of sweetpotato root starch by endogenous amylases (Regal variety)
Figure 3B:
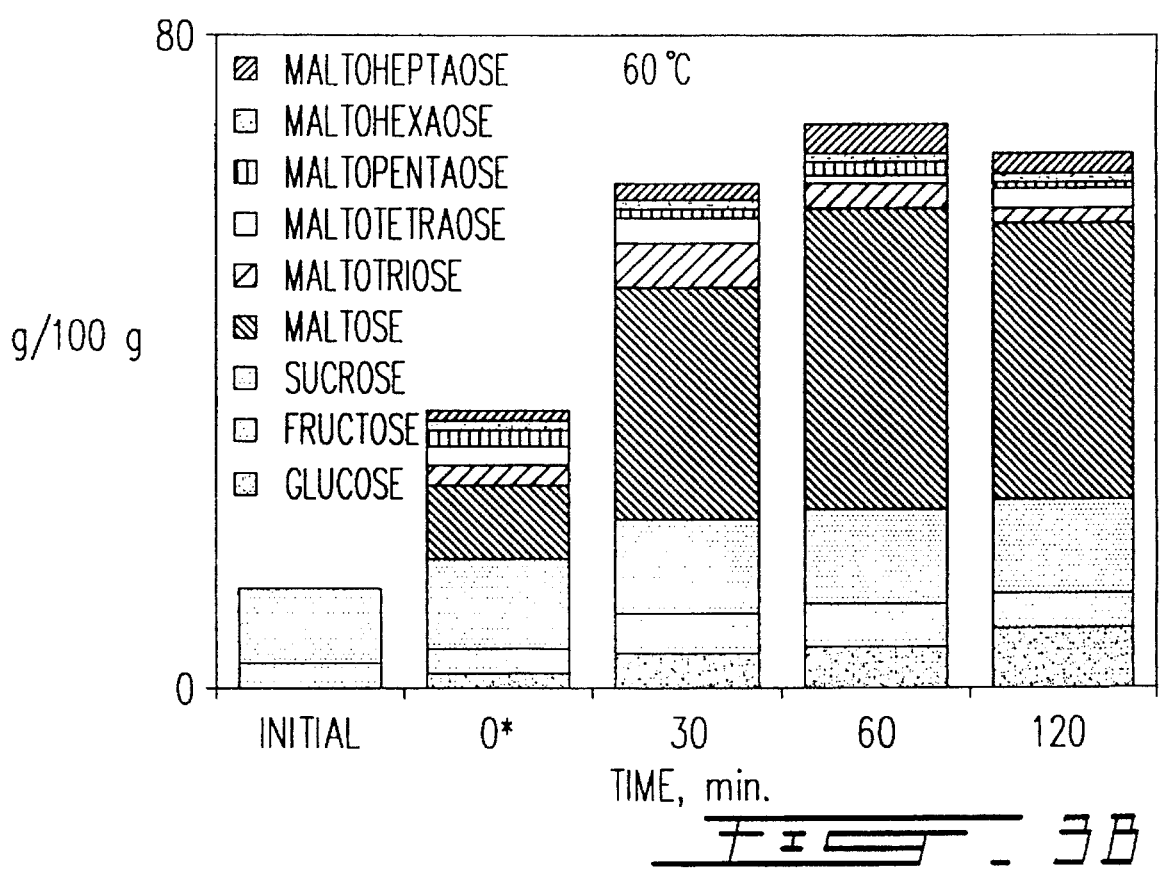
Figure 3C:
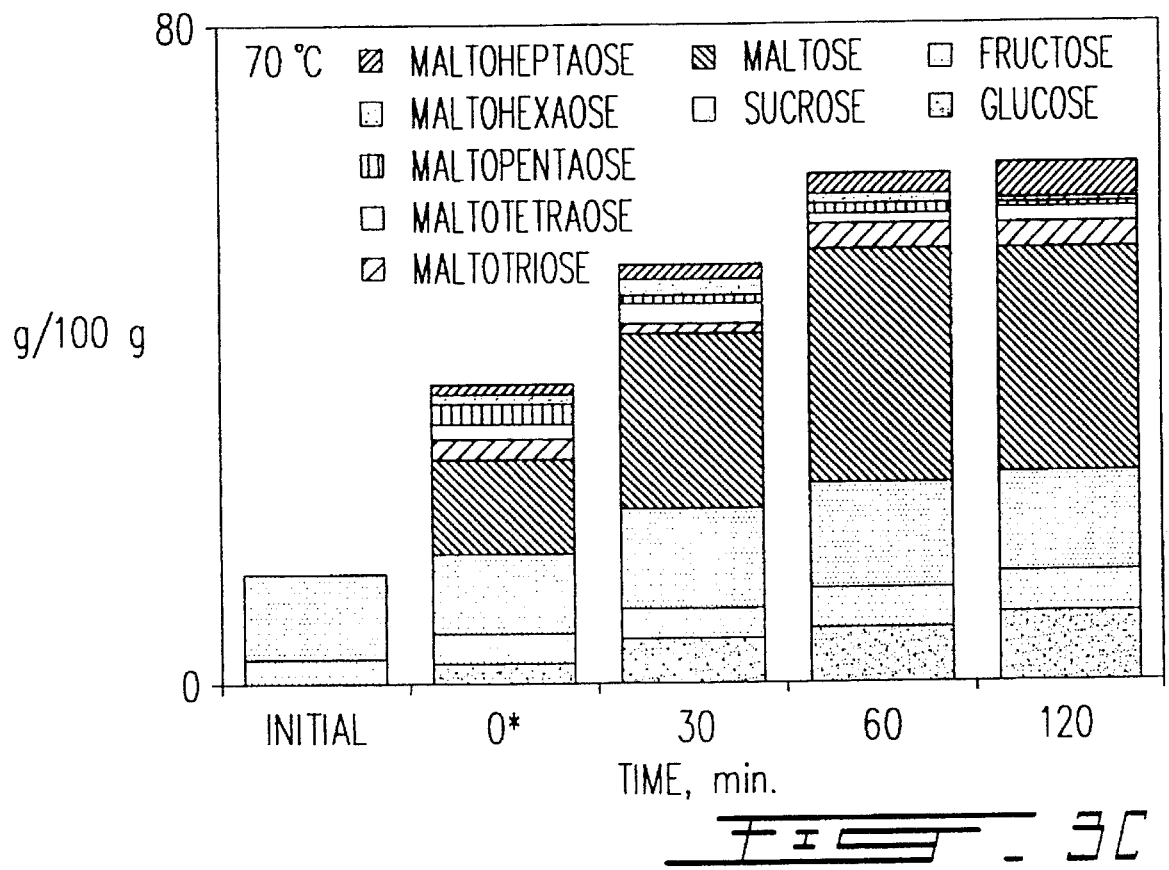
Figure 3D:
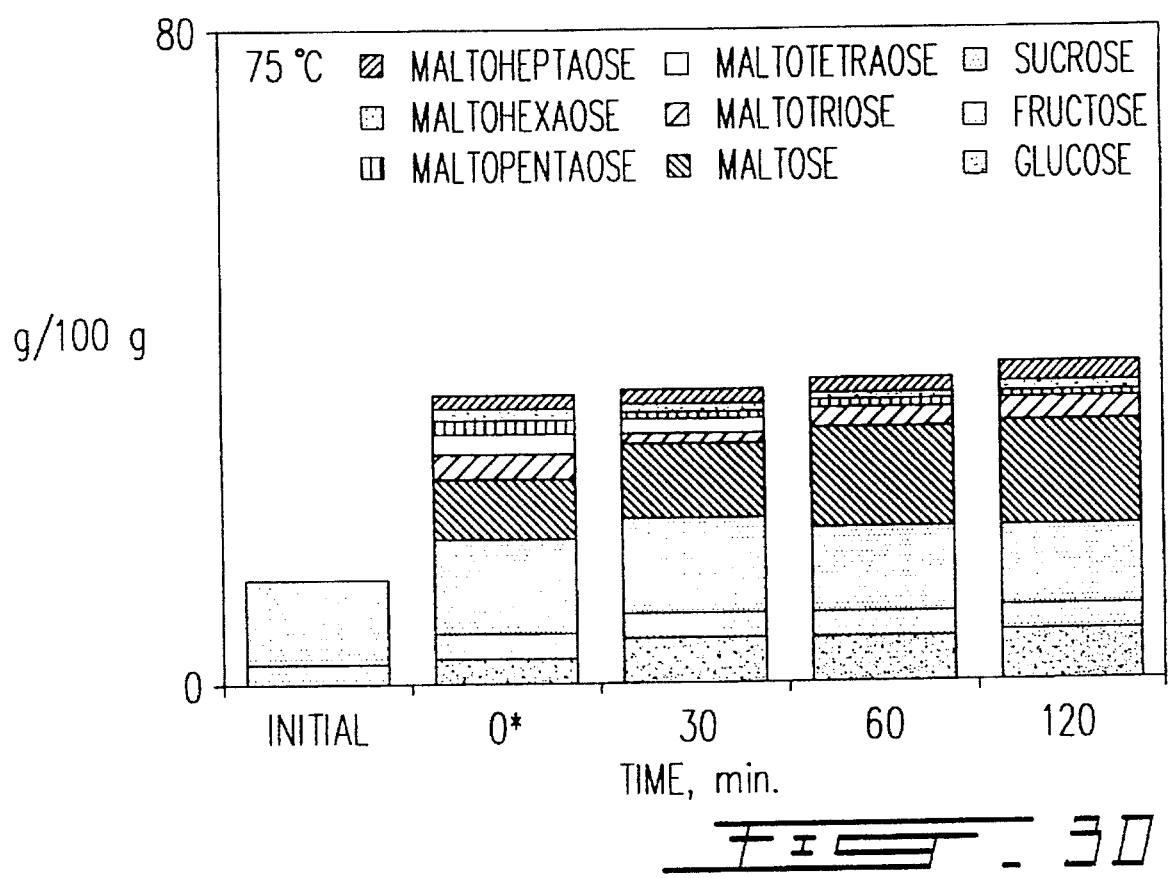

A large amount of sweetpotato root starch was hydrolyzed by the addition of extract from the outer tissues of the root to the heated and previously tempered root inner portion slurry. Data of changes in concentrations of starch and reducing sugars are shown in FIG. 2. 0* min. time represent the data monitored immediately after mixing the heated and appropriately tempered inner root portion with the outer tissue extract. For Regal variety (FIG. 2A), a large amount of starch was converted at 70° C., where 70% (based on fresh weight) were hydrolyzed in low molecular weight products after 60 min. of inner slurry incubation with outer tissue extract. The highest levels of total reducing sugars were obtained at 70° C. and 60° C. while the lowest were at 50° and 75° C. For White Delight cultivar, there was no difference between three temperatures used, and starch hydrolyzed after 60 min. represented 50% of initial root starch (FIG. 2B). The starch content for White Delight was higher than for Regal and the reducing sugar amount realized after 1 h. incubation was higher for White Delight than for Regal at each temperature considered.

Otherwise, the starch decrease during the first minute of incubation may be due to the action of the crude extract containing both $\alpha$- and $\beta$-amylases, that were also found by Maeda et al. (Maeda, I. et al., 1978, Agric. Biol. Chem., 42: 259–267) to be very quick and effective in starch digestion.

Figure 4A:
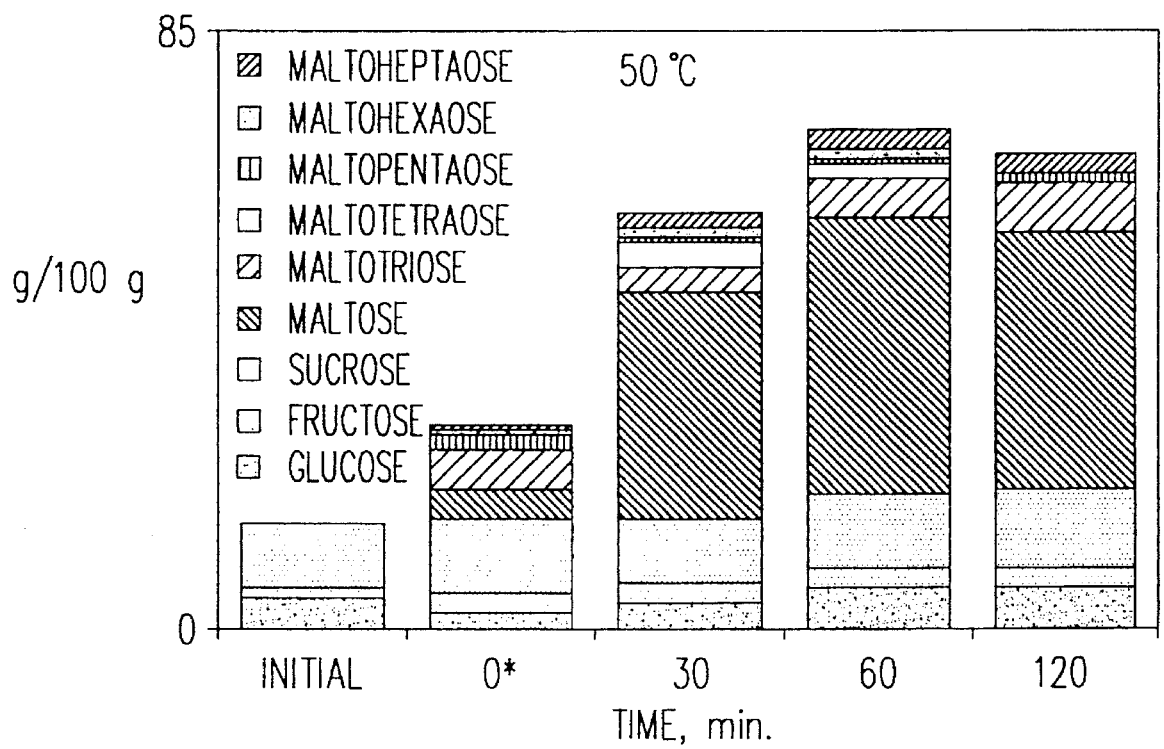
FIG. 4 illustrates the changes in sugar and oligodextrin content during digestion of sweetpotato starch by endogenous amylases (White Delight variety)
Figure 4B:
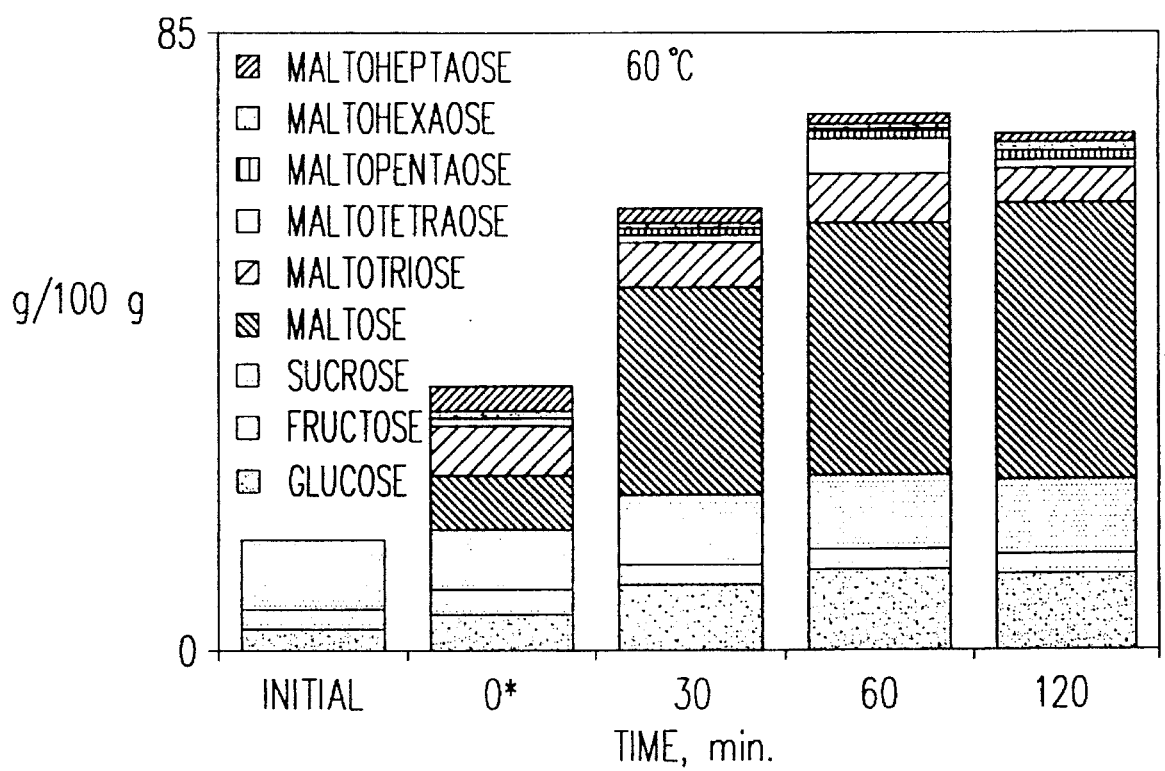
Figure 4C:
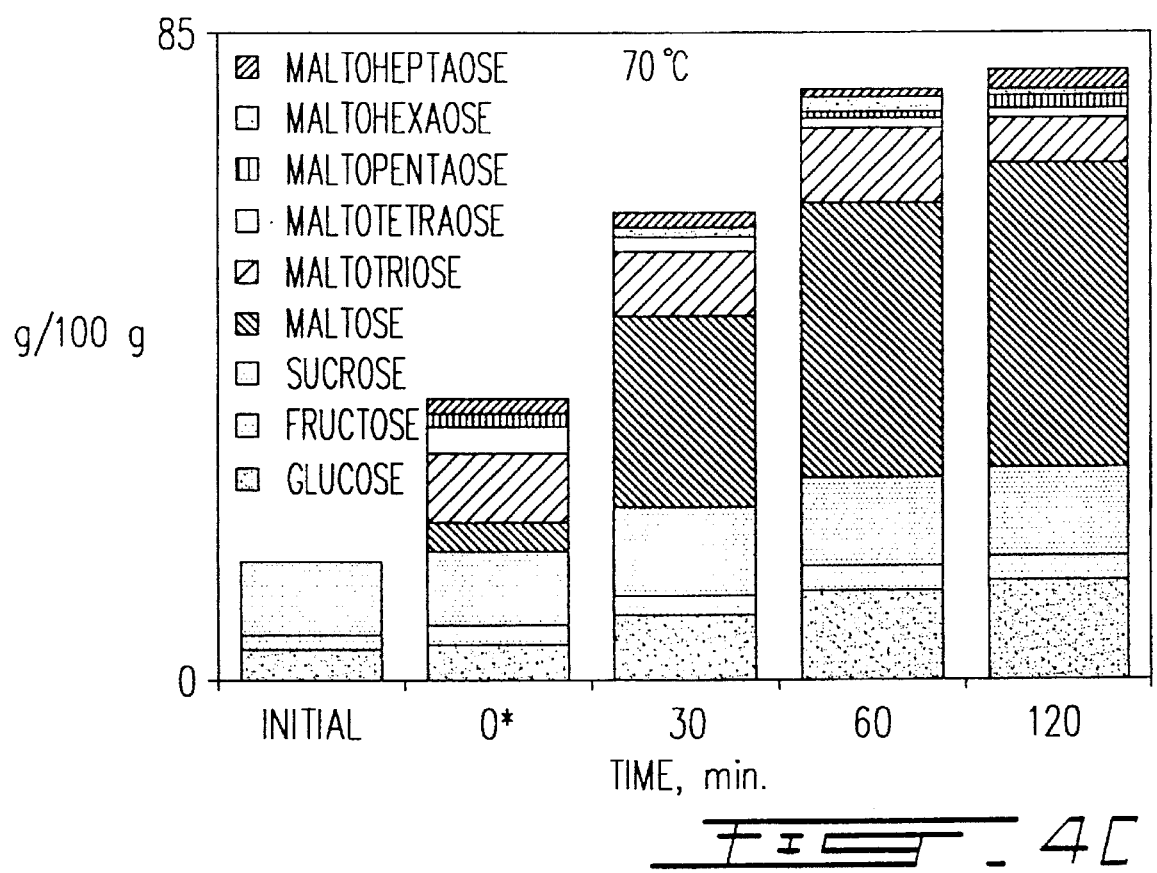
Figure 5A:
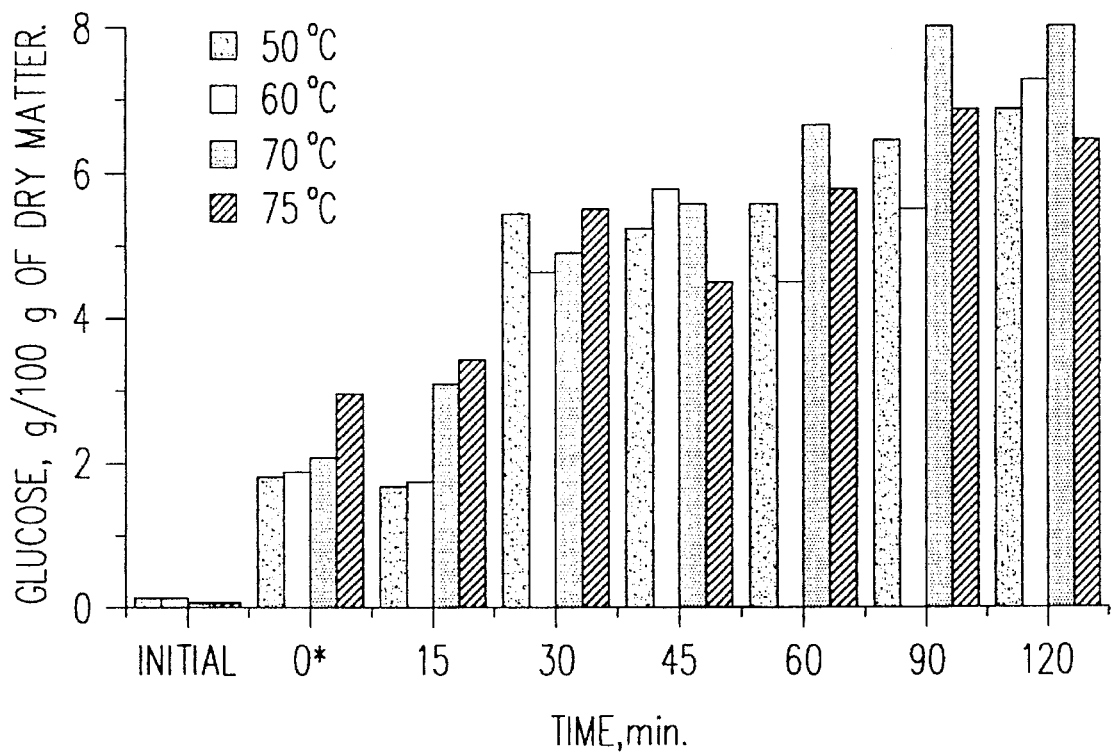
FIG. 5 illustrates the changes in glucose content during digestion of sweetpotato starch by endogenous amylases for Regal (A) and White Delight (B) varieties.
Figure 5B:
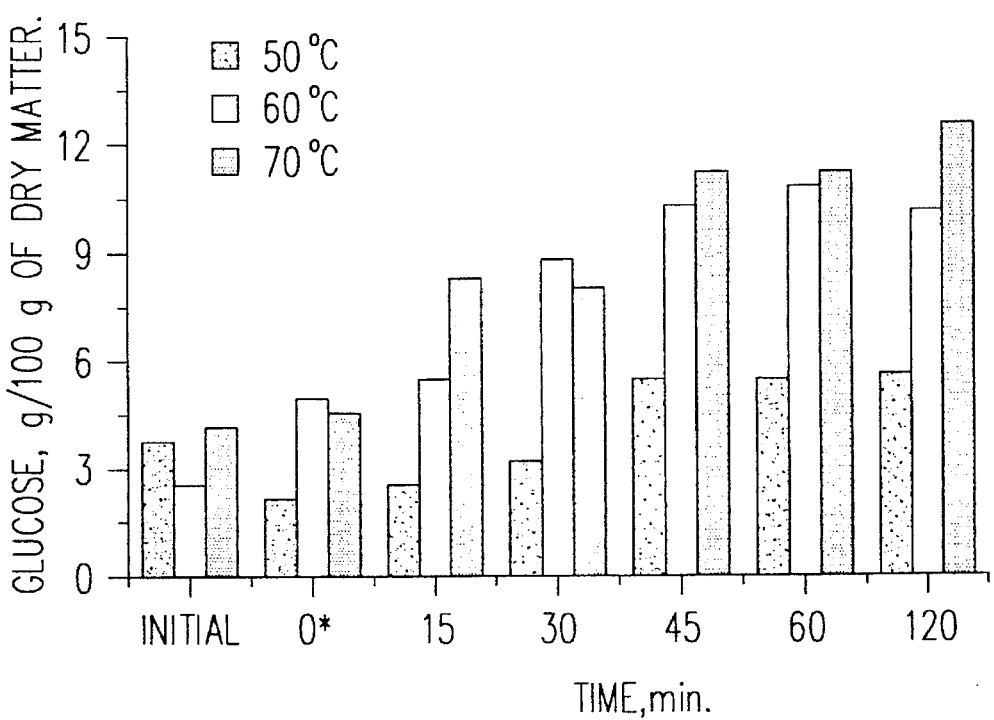
Figure 6A:
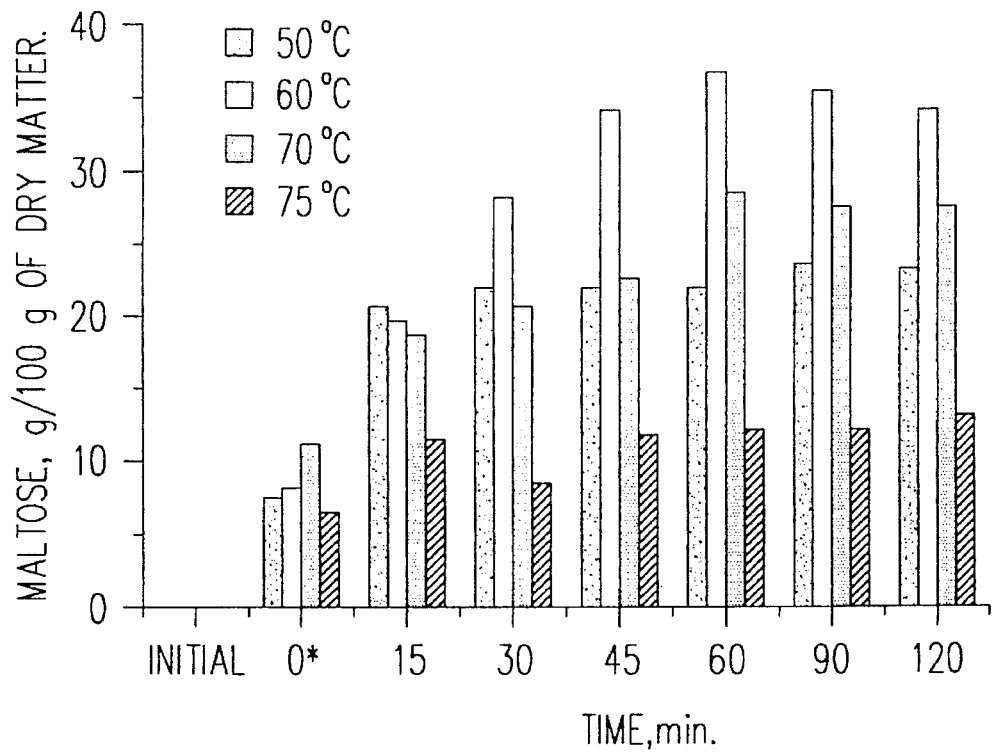
FIG. 6 illustrates the changes in maltose content during digestion of sweetpotato starch by endogenous amylases for Regal (A) and White Delight (B) varieties.
Figure 6B:
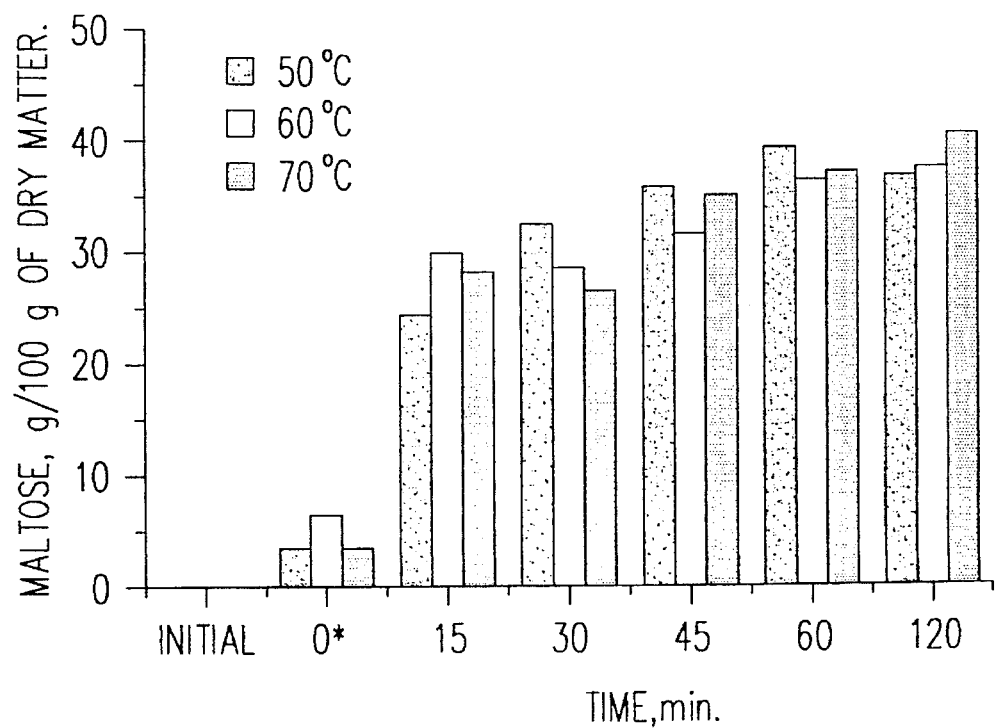

Sweetpotato extract containing both $\alpha$- and $\beta$-amylase produced along with glucose (FIG. 5) and maltose (FIG. 6), a series of oligodextrins (maltotriose, maltotetraose, maltopentaose, maltohexaose and maltoheptaose) (FIGS. 3 and 4).

Moisture determination

Triplicate 10 g samples were weighed to 0.1 mg, dried for 48 h. at 70° C. in a forced-air oven, removed, allowed to cool for 5 min. in a desiccator, and again weighed.

Chemical analysis 5 ml water were added to each 4 g sample and centrifuged for 10 min. at 2,500×g. 500 µl were withdrawn, stored at −20° C. and used for further HPLC sugars determination. 5 ml water were again added to each sample and vortexed. After a centrifugation for 10 min. at 2,500×g, an appropriate aliquot was withdrawn for determination of reducing sugars (as glucose equivalent) using p-hydroxy-benzoic hydrazide procedure of Blakeney and Mutton (Blakeney, A. B. et al., 1980, J. Sci. Food Agric., 31: 889–897). The mixture was vortexed and tempered at 55° C. for 30 min., and 5 ml of 0.01 M Na-acetate (pH 4.5) containing 10 units/ml of amyloglucosidase (Sigma N° A-7255) were added to each sample. Samples were maintained at 55° C. for 60 min. and appropriate aliquot withdrawn for determination of reducing sugars realized as above. The difference between samples treated and those non-treated with amyloglucosidase was considered as starch after calculation as described by Rose at al. (Rose, R. et al., 1991, J. Agric. Food Chem., 39: 2–11).

HPLC sugar determination

The HPLC system was a Waters™ 6000 A pump (Waters, Milford, Mass.), a Waters™ 410 refractive index detector, a Rheodyne™ 7125 injector (Rheodyne, Cotati, Calif.), and a Bio-Rad Amino-5S™ column (Bio-Rad Laboratories, Richmond, Calif.) 4 mm i.d.×25 mm in length. The mobile phase was 65 acetonitrile: 35 water (v/v), and the flow rate was 1.0 ml/min. Quantitation of the sugars was accomplished with a Shimadzu™ C-R3A integrator (Shimadzu Scientific Instruments, Columbia, Md.). Peak identity and sugar abundance were obtained by comparison to standards. Standards of maltose, maltotriose, maltotetraose, maltopentaose, maltohexaose, and maltoheptaose were purchased from Sigma Chemical Co. (St. Louis, Mo.). Glucose, fructose and sucrose were obtained from Fisher Scientific Co. (Montréal, Canada). 0.1% (w/v) standards were prepared to assist in identifying sugars and oligosaccharides present in slurry.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A method for the hydrolysis of sweetpotato starch to form a puree which comprises the steps of:

a) separating outer and starchy inner tissues of sweetpotato roots;

b) heating said separated starchy inner tissues of step a) for a time sufficient for obtaining a suitable starch slurry;

c) preparing an amylase crude extract from sweetpotato roots outer tissues of step a); and d) incubating said slurry of step b) with said extract of step c) for a time sufficient for the hydrolysis of said starch.

2. The method of claim 1, wherein said heating of step b) is conducted for a time of about 20 min. to about 2 hours.

3. The method of claim 1, wherein said separation of step a) is a mechanical separation which comprises removing the outer tissues from the sweetpotato root up to about 0.1 to about 0.5 cm deep.

4. The method of claim 1, wherein said preparation of crude extract of step c) is effected by centrifugation at about 500×g to about 15,000×g for about 5 min. to about 1 hour.

5. The method of claim 4, wherein said crude extract of step c) comprises endogenous α- and β-amylases.

6. The method of claim 1, wherein said incubating of step d) is conducted for a time of about 30 min. to about 4 hours.

* * * * *